(12) United States Patent
Rushbrooke et al.

(10) Patent No.: US 7,502,442 B2
(45) Date of Patent: Mar. 10, 2009

(54) X-RAY INSPECTION SYSTEM AND METHOD

(75) Inventors: John Gordon Rushbrooke, London (GB); Justin Rushbrooke, legal representative, London (GB); Claire Elizabeth Hooper, Cambridge (GB)

(73) Assignee: Smiths Heimann GmbH, Wiesbaden (DE)

( * ) Notice: Subject to any disclaimer, the term of this patent is extended or adjusted under 35 U.S.C. 154(b) by 0 days.

(21) Appl. No.: 10/501,616

(22) PCT Filed: Jan. 28, 2002

(86) PCT No.: PCT/GB02/00353

§ 371 (c)(1),
(2), (4) Date: May 25, 2005

(87) PCT Pub. No.: WO03/065023

PCT Pub. Date: Aug. 7, 2003

(65) Prior Publication Data

US 2006/0011848 A1 Jan. 19, 2006

(51) Int. Cl.
*G01N 23/04* (2006.01)
*H05G 1/62* (2006.01)
*G01T 1/202* (2006.01)

(52) U.S. Cl. .................. 378/57; 378/98.12; 250/369

(58) Field of Classification Search ............. 378/53, 378/57, 65, 147, 154, 51, 98.12; 356/437; 250/361 R, 393, 394, 358.1, 363.01, 370.06, 250/370.11, 370.12, 366–369

See application file for complete search history.

(56) References Cited

U.S. PATENT DOCUMENTS 3,399,302 A * 8/1968 Carrell ................. 250/390.04

(Continued)

FOREIGN PATENT DOCUMENTS

EP 0162321 A1 11/1985

(Continued)

OTHER PUBLICATIONS

Maeda, "Development of an in-air high-resolution PIXE system", Nuclear instruments and Methods in Physics Research, vol. 134, No. 3-4, Mar. 1, 1998, pp. 418-426.

(Continued)

*Primary Examiner*—Edward J Glick
*Assistant Examiner*—Anastasia Midkiff
(74) *Attorney, Agent, or Firm*—Barnes & Thornburg LLP

(57) ABSTRACT

An X-ray inspection system in which a thin X-ray absorber is placed upstream of an object under investigation so as to remove low energy X-rays, typically below 0.5 MeV. The absorber may be a sheet of lead 10 mm thick. Where the X-ray inspection system which incorporates a detector which relies on the electro-magnetic cascade effect produced in suitable materials when bombarded with X-rays so that energy is transferred into the material at different depths depending on the energy of incident X-rays, and the first component on which the X-rays impinge comprises a relatively thin crystal this unwanted background may be reduced by placing a vessel containing a fluid whose density is less than that of air, in front of the detector crystal array. Typically the fluid is helium at atmospheric or slightly greater than atmospheric pressure. The background can be reduced by applying a magnetic field in the region in front of the detector crystal array so as to sweep away electrons from that region.

7 Claims, 3 Drawing Sheets

U.S. PATENT DOCUMENTS

| | | | | |
|---|---|---|---|---|
| 3,539,806 A * | 11/1970 | Humphrey | ................. | 250/366 |
| 3,873,838 A * | 3/1975 | Lee | ............. | 250/366 |
| 4,053,767 A * | 10/1977 | Kampfer et al. | .......... | 250/252.1 |
| 4,413,353 A * | 11/1983 | Macovski et al. | ............. | 378/62 |
| 4,511,799 A * | 4/1985 | Bjorkholm | ................. | 250/367 |
| 4,571,491 A | 2/1986 | Vinegar | | |
| 4,578,803 A * | 3/1986 | Macovski | .................... | 378/62 |
| 4,618,773 A * | 10/1986 | Drukier | ................. | 250/363.02 |
| 4,651,006 A | 3/1987 | Valenta | | |
| 4,677,299 A * | 6/1987 | Wong | ................... | 250/363.03 |
| 4,687,935 A | 8/1987 | Nurmi | | |
| 4,700,072 A | 10/1987 | Pikari | | |
| 4,772,792 A | 9/1988 | Utts | | |
| 4,887,604 A * | 12/1989 | Shefer et al. | ................ | 600/431 |
| 4,933,960 A | 6/1990 | Fujisaki | | |
| 5,044,002 A | 8/1991 | Stein | | |
| 5,138,167 A * | 8/1992 | Barnes | ................. | 250/370.01 |
| 5,319,547 A | 6/1994 | Krug | | |
| 5,374,824 A * | 12/1994 | Chaney et al. | ......... | 250/363.02 |
| 5,393,981 A | 2/1995 | Szabo | | |
| 5,420,441 A * | 5/1995 | Newman et al. | ............ | 250/581 |
| 5,493,596 A | 2/1996 | Annis | | |
| 5,514,870 A * | 5/1996 | Langenbrunner | .......... | 250/367 |
| 5,517,544 A * | 5/1996 | Levinson | ...................... | 378/4 |
| 5,524,133 A * | 6/1996 | Neale et al. | ................... | 378/53 |
| 5,692,029 A * | 11/1997 | Husseiny et al. | ............. | 378/88 |
| 5,712,483 A * | 1/1998 | Boone et al. | ................. | 250/367 |
| 5,753,917 A * | 5/1998 | Engdahl | .................... | 250/367 |
| 5,768,334 A | 6/1998 | Maitrejean | | |
| 5,793,046 A | 8/1998 | Jeffers | | |
| 5,813,983 A * | 9/1998 | DiFilippo et al. | ........... | 600/407 |
| 5,923,722 A * | 7/1999 | Schulz | ...................... | 378/98.8 |
| 5,960,057 A * | 9/1999 | Majewski et al. | ............ | 378/62 |
| 6,078,052 A * | 6/2000 | DiFilippo | .................. | 250/367 |
| 6,087,663 A * | 7/2000 | Moisan et al. | .............. | 250/367 |
| 6,088,423 A | 7/2000 | Krug | | |
| 6,151,381 A * | 11/2000 | Grodzins et al. | ............. | 378/90 |
| 6,294,791 B1* | 9/2001 | Williams et al. | ....... | 250/455.11 |
| 6,534,771 B1* | 3/2003 | Rozsa | ....................... | 250/367 |
| 6,542,580 B1* | 4/2003 | Carver et al. | .................. | 378/57 |
| 6,570,160 B1* | 5/2003 | Maekawa et al. | .......... | 250/367 |
| 6,653,637 B2* | 11/2003 | Ochiai et al. | ................ | 250/397 |
| 6,920,203 B2* | 7/2005 | Short et al. | .................. | 378/147 |
| 7,286,640 B2* | 10/2007 | Yun et al. | .................. | 378/98.9 |
| 2003/0030003 A1* | 2/2003 | Maekawa et al. | .......... | 250/367 |
| 2003/0076924 A1* | 4/2003 | Mario et al. | .................. | 378/57 |
| 2003/0204126 A1* | 10/2003 | Rivard | ........................... | 600/3 |

FOREIGN PATENT DOCUMENTS

| | | |
|---|---|---|
| EP | 0204365 A2 | 12/1986 |
| GB | 884789 B | 12/1959 |
| GB | 1332370 B | 10/1973 |
| GB | 2091417 A | 7/1982 |
| GB | 2149193 A | 6/1985 |
| GB | 2196113 A | 4/1988 |
| GB | 2295454 A | 5/1996 |
| GB | 2297835 A | 8/1996 |
| JP | 56111438 A | 9/1981 |
| JP | 5716744 A | 10/1982 |
| SU | 19813355509 | 11/1981 |
| WO | WO93/14419 A1 | 7/1993 |
| WO | WO-01/09596 A1 | 2/2001 |

OTHER PUBLICATIONS

Kalinin, "investigation of Positron Generation by Relativeistic Electrons in Aligned Crystals", Nuclear Instruments and Methods in Physics Research, vol. 145, No. 1-2, Oct. 2, 1998j pp. 209-220.

* cited by examiner

X-RAY INSPECTION SYSTEM AND METHOD

FIELD OF INVENTION

This invention concerns X-rays inspections systems and methods of X-ray inspection by which the mean atomic number of material in an object under test can be determined. The invention is of particular application in the field of baggage container checking at ports, airports, railway marshalling yards and the like, but is not limited to these applications and may be used in medical diagnosis and non-destructive testing.

BACKGROUND TO THE INVENTION

It is known to use X-rays for transmission imaging in baggage scanning facilities at airports and the like.

EP 0621959 describes a method and apparatus for X-ray inspection using high energy X-rays which permit discrimination on the basis of atomic number between materials exposed to the X-rays.

It also describes a method and apparatus by which the contents of objects such as steel shipping containers as used for road, rail and maritime freight, can be X-rayed and a mean atomic number profile generated of the contents for the analysis using conventional image analysis techniques. These methods and apparatus have been used to identify the presence of particular substances or combinations of substances within a container, whereby an alarm signal is generated if one or more criteria is satisfied so as for example to prevent the loading or subsequent transit of a container so identified.

In a preferred method as aforesaid for detecting the mean atomic number of a mass of material in an object (typically within a container and therefore hidden from view), comprises the steps of:
1. subjecting the material to high energy X-rays and determining the mean number $N_A$ of X-rays transmitted through the region thereof,
2. subjecting the same region of the material to X-rays having a significantly higher energy than the first mentioned X-rays and determining the mean number $N_B$ of the higher energy X-rays transmitted therethrough,
3. computing the value of the ratio $N_A$ to $N_B$, and
4. determining from a look-up table and delivering as an output the average atomic number corresponding to the computed value of the $N_A/N_B$ ratio.

By significantly higher is meant at least twice and typically five or six times or more the energy of the first mentioned high energy X-rays. Thus if the lower high energy X-rays are of the order of 1 MeV, the higher energy X-rays will be typically of the order of 5 or 6 MeV.

A preferred embodiment of the invention described in EP 0621959 comprises a single broad energy band X-ray source which projects a range of high energy X-rays of 1 MeV and above, towards the object; a composite detector which is placed beyond the object, and which on bombardment by transmitted X-rays produces substantially simultaneously:
a. a first component predominantly attributable to the higher energy component of the incident X-rays and
b. a second component predominantly attributable to the lower energy component of the incident X-rays;

circuit means adapted to determine the light generated in scintillating crystals by the said two components; means for generating therefrom numerical values relating thereto; means for forming a ratio of one numerical value relative to the other; and a look-up table of atomic numbers and ratio values, the mean atomic number for material through which the X-rays have passed can be derived using the derived value of the said ratio, for the material in question.

SUMMARY OF THE INVENTION

According to one aspect of the present invention, a thin X-ray absorber is placed upstream of the object so as to remove low energy X-rays.

Material discrimination is reversed at low energies (as in a baggage scanner which uses X-rays of approximately 100 keV), and so a very low energy component in the beam will dilute or weaken any material discrimination at higher energies.

One form of absorber is lead and typically a sheet is used some 10 mm thick. This removes X-rays below 0.5 MeV.

Practical composite detectors are described in EP 0621959 and one such detector relies on the electro-magnetic cascade effect produced in suitable materials when bombarded with X-rays. In such arrangements energy is transferred into the material at different depths depending on the energy of incident X-rays.

In one such detector the first component on which the X-rays impinge comprises a relatively thin crystal so that the energy deposited is more or less independent of X-ray energy, and the spectrum of sample X-rays is therefore strongly peaked in the range 1 MeV to 1.5 MeV. The thin crystal is followed by a low-Z beam hardener which preferentially removes lower energy X-rays from the beam. The surviving X-rays are then transmitted to a series of high-Z converters (which favour pair production), which alternate with and are thereby sandwiched, by thin crystals, which sample the electrons produced by collisions upstream of the crystals. The higher the energy the further downstream will occur collisions which can be sampled, thus enhancing the probability of detection of the higher energy X-rays. Increasing the proportion of pair production increases the average energy of secondary electrons.

Light from the crystals in such a detector is conveyed to a photo-electric device. The device may be a photodiode, a CCD camera or an intensified CCD camera or any other device for converting light energy into electrical energy, and where appropriate optical fibres may be used to couple the crystals to the light sensitive devices.

In such a detector the front crystal (which is usually relatively thin) has to preferentially respond to lower energy X-rays in the range 1 to 1.5 MeV. This relies on an X-ray traversing the thin crystal and depositing only a small amount of its energy. However background energy (mainly electrons) can strike the front crystal and cause it to respond to higher amounts of energy and hence weaken the material discrimination capability. An important source of such background is electrons coming from X-ray interactions in the air just upstream of the detector array. Typically within a range of 0.5 m of the array.

According therefore to another aspect of the invention, this unwanted background can be reduced by placing a vessel containing a fluid whose density is less than that of air, in front of the detector crystal array. The vessel may comprise a bag, typically formed from film transparent to X-rays.

A preferred fluid is helium.

The fluid may be maintained at atmospheric or slightly greater than atmospheric pressure.

The reduction in background electrons is achieved because the number of X-ray interactions in a gas is proportional to its density. Since the density of helium is approximately one seventh that of air, there will be a proportionately reduced number of interactions and therefore a lower background electron activity.

According to a further aspect of the invention, the background can be reduced by applying a magnetic field in the region in front of a detector crystal array so as to sweep away electrons from that region.

The invention thus also provides a material discrimination detector such as described in EP 0621959 in combination with either or both of a vessel such as a bag containing low density fluid and means for generating a magnetic field, in front of the detector array.

According to another aspect of the invention, electrons and scattered X-rays may be removed by positioning collimators in front of the detector crystal array of a material discrimination system such as described in EP 0621959.

Typically lead collimators are employed.

In a material discrimination system as described in the aforementioned European patent specification, the first detector component is a thin scintillation crystal which is required to register an amount of energy deposited by an X-ray that is essentially independent of the X-ray MeV energy, and in accordance with a still further aspect of the present invention, it has now been observed that the low Z converter located after this crystal to preferentially remove lower energy X-rays, additionally stops electrons produced by X-ray interactions downstream of the crystal from being significantly back scattered into the front crystal, and prevents electrons leaving the front crystal from returning and depositing more energy in the front crystal.

A preferred material for the low Z converter is aluminium.

The invention thus also comprises a material discrimination system in which a low-Z converter typically of aluminium is located downstream of the first scintillating crystal detector to prevent electrons produced by X-ray interactions downstream of the said first crystal from back scattering into the first crystal and prevent electrons from leaving the first crystal and returning thereto.

A material discrimination system as described in the aforementioned European patent specification may therefore further comprise a low-Z converter situated between a thin front scintillation crystal and a thicker downstream scintillation crystal, typically formed from aluminium, and adapted to reduce the back scatter of electrons into the front crystal and to prevent electrons which have left the front crystal from returning thereto.

Preferably behind the low-Z converter is located a high-Z, high density convertor whose main purpose is to ensure that even the higher MeV energy components of an X-ray beam lose energy at the maximum rate so that the electro-magnetic cascade reaches equilibrium, to ensure that the maximum amount of energy per X-ray is deposited in the following crystal, so that it will respond preferentially to higher energy X-rays.

The high Z material is preferably tungsten.

Electrons travelling backwards out of the said crystal as the result of multiple Coulomb scatter, are absorbed in both the low and high-Z converters so that they are unable to reach the thin front crystal.

According to a development of this last aspect of the invention, high-Z, high density converters, may be interleaved with scintillating crystals, each crystal being read out for example by a pair of photodiodes or fibres or the like.

Signals from all such pairs of read out devices may be added.

This increases still more the effective energy of the high energy X-ray component that is registered, and hence the magnitude of the material discrimination effect.

According to a further development of this aspect of the invention, at the rear of the detector assembly an absorber is located, the purpose of which is to stop electrons produced by X-rays which are carrying on downstream and scattering in material such as the back wall of a building housing the apparatus, from reaching the rear crystal of the detector array.

Typically the absorber is aluminium.

According to a further feature of the invention, the thin front crystal in a material discrimination detector such as described in the aforementioned European patent may be read out from each side as by a photodiode, or fibre, and the outputs from the two opposite sides of the crystal may then be added. This prevents any left/right asymmetry in signal that results from reading out at one end only, with respect to direction of motion of the object.

According to another aspect of the invention, in an arrangement comprising a front thin crystal and a rear thick crystal, the latter is preferably read out by several photodiodes or fibres or other devices which sample at different depths in the beam direction and the signals from the different sampling devices may be added to represent the high energy X-ray component. Again outputs from the two sides of the crystal may be combined to prevent left/right asymmetry.

Where the second crystal is replaced by a sandwich of alternating crystals and high-Z convertors, each of the crystals in the sandwich may be read out using two or more read-out devices again with the outputs from opposite sides being combined to prevent left/right asymmetry such as by fibres leading to CCD cameras or photodiodes and all of the read-outs may be combined to produce a signal corresponding to the high energy X-ray component.

When constructing a material discrimination detector such as described in the aforementioned European patent, the front and rear scintillation crystals are preferably cut from the same ingot of material in order to provide matched performance. In the case of CsI material, the choice of material should also seek to minimise persistence of the signal due to low phosphorescence decay.

According to another aspect of the invention, in a material discrimination system as described in the aforementioned European patent which includes a Linac, the read-out system is preferably synchronised to the Linac pulse, with one read-out cycle for each pulse.

According to a preferred feature of this aspect of the invention, the read-out system may also sample the output from crystals between each Linac pulse, so as to provide signals indicative of noise and crystal persistence.

In a system in which beam flux allows it, the Linac may be triggered on each alternate pulse only, and during non-beam read-outs, signals corresponding to background, noise and crystal persistence, may be subtracted.

According to a further aspect of the invention, in a material discrimination system as described in the aforementioned European patent and which incorporates a Linac, the channels are preferably normalised so as to overcome the non-linear effects due to saturation.

Preferably calibration is performed by increasing the X-ray beam flux by known increments. However this is difficult in practice and the beam spectrum (energy and angular dependent) can depend on Linac beam current.

According to a further feature of the invention, a step wedge of suitable material is incorporated with increments of thickness chosen to yield fixed decrements of transmission between 90% and 10% when used with a 10 MeV Linac. In accordance with this aspect of the invention, a method of calibration involves moving the step wedge across the X-ray beam and determining the average signal value vs step thickness for use as a base level for channel to channel normalisation.

A preferred material for the step wedge device is PTFE.

According to a further feature of the invention, material discrimination is performed by generating calibration curves of material discrimination effect (MD) verses transmission T. Typically T is 1 for zero absorbtion and 0 for completely absorbing objects. The MD effect is derived from the lower and high energy signals and calibration is performed as aforementioned using step wedges of suitable material. In order to produce a range of curves for calibration, different materials are used such as PTFE, aluminium and iron and the effective Z of an unknown material is then found by comparing its MD effect and T with the corresponding values of known materials and then interpolating.

It has been noted that the effective Z of a material may be different depending on whether high or low energy X-rays are employed. Thus at energies well below 1 MeV the effective Z of a material may be different than if X-rays having energies much greater than 1 MeV are employed. As an example, cocaine has an effective Z of 9.4 at relatively low energy X-rays such as used in conventional baggage scanners, but a lower value of 6.8 for X-rays above 1 MeV.

Apparatus as described in the aforementioned European patent and as modified herein may be used for medical and non-destructive testing purposes. In the case of radio therapy, X-ray energies in the range 18 to 25 MeV may be employed where the MD effect is stronger.

The invention will now be described by way of example, with reference to the accompanying drawings, in which.

Figure 1:
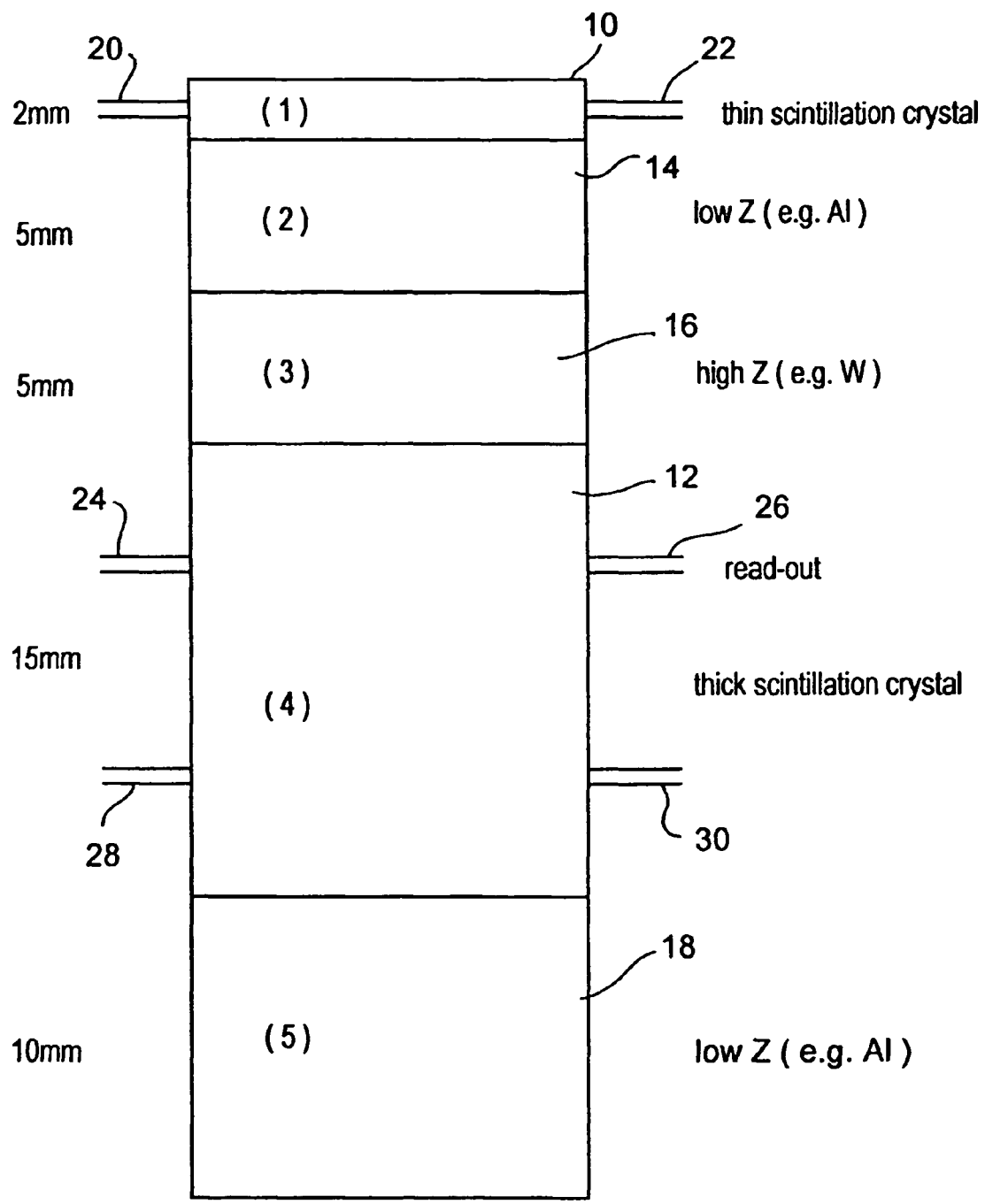
FIG. 1 is a modified detector element.

In FIG. 1 a detector is shown in diagrammatic form constructed in accordance with the present invention.

The first element comprises a thin scintillating crystal 10. The second detecting element is a much thicker scintillating crystal 12 but between the two crystals are located first a low-Z convertor such as aluminium shown at 14 followed by a high-Z material such as W shown at 16. If the first crystal has a thickness of 2 mm, the second thicker crystal will typically have a thickness of 15 mm and each of the two convertors 14 and 16 will be typically 5 mm thick.

In accordance with the invention, a low-Z absorption layer is provided to the rear of the second crystal 12 and this is denoted by reference numeral 18. Typically this is formed from aluminium and will be of the order of 10 mm thick.

In order to reduce asymmetry, two read-outs are provided from opposite sides of the thin crystal 10, one at 20 and the other at 22. Each typically comprises a photodiode or a fibre optic leading to a photo detector such as a CCD camera, or any combination thereof. It is to be understood however that the invention is not limited to the use of any particular read-out device, and any device capable of converting light energy to electrical energy for generating an electrical signal whose magnitude in proportion to the amount of light produced is appropriate. Nor is the invention limited to the use of two light sensitive detecting devices to reduce asymmetry, where one or more than two light detectors, will also reduce asymmetry.

In the case of the thicker crystal, two pairs of read-out devices are employed denoted by 24 and 26 at the front end of the crystal and 28 and 30 at the rear end of the crystal.

In theory, many read-out devices can be accommodated on the two opposite side faces of the crystal such as 12, and the two pairs shown in FIG. 1 are merely exemplary. It will be appreciated that the more light sensitive read-out devices which are coupled to the crystal, the greater will be the number of electrical signals resulting from a light emitting event for combination.

Figure 2:
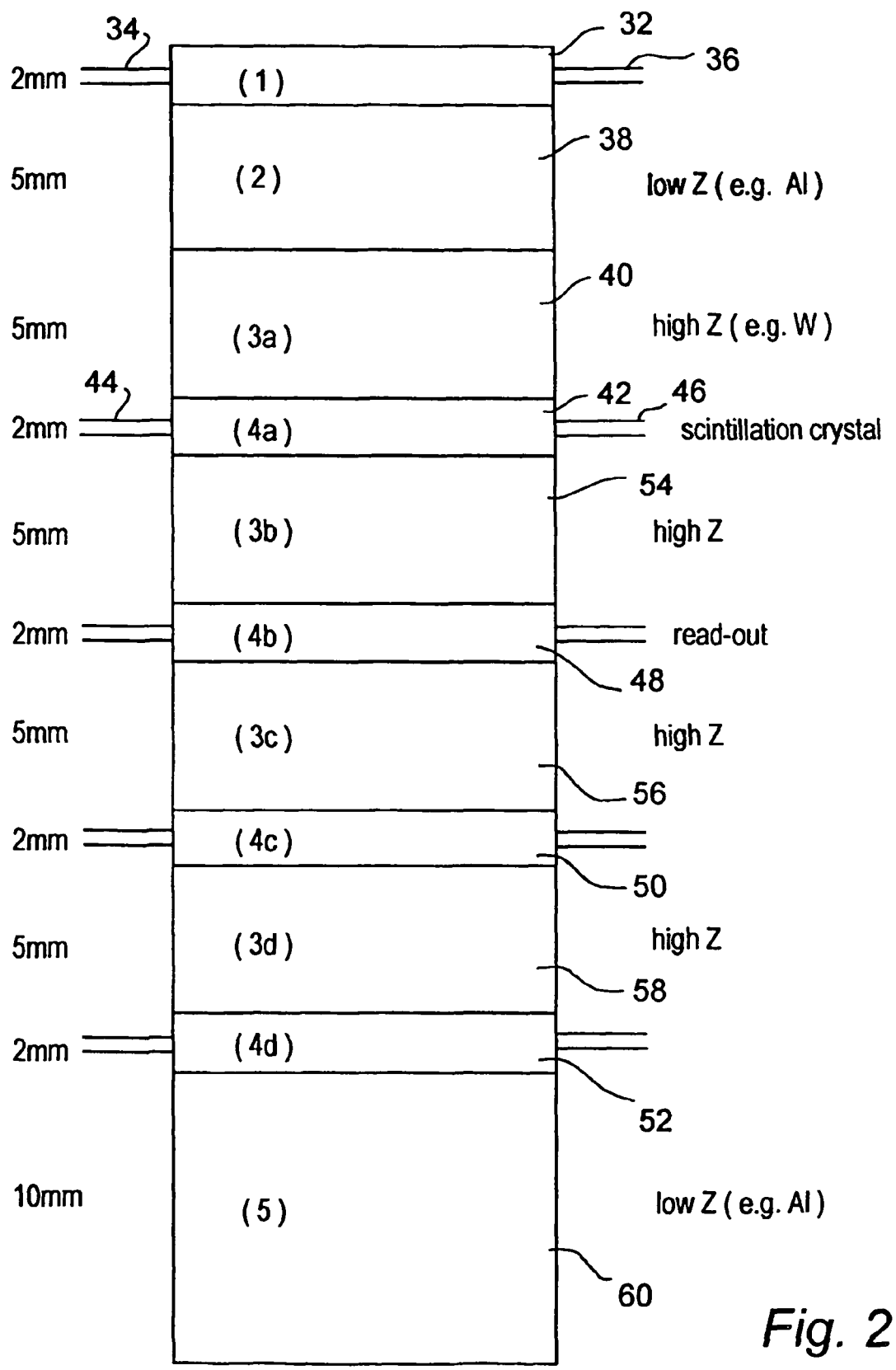
FIG. 2 is a further modified detector element.

In FIG. 2 the input crystal comprises a thin crystal 32 typically of 2 mm thickness and having opposite read-outs at 34 and 36. Low and high-Z materials are provided at 38 and 40 in the same way as in FIG. 1, typically of aluminium and W between the front crystal 32 and the first of a series of second crystals which is denoted by reference numeral 42.

The thickness of each of the low and high-Z elements 38 and 40 is typically 5 mm.

The crystal 42 is, like the first crystal 32, read out from opposite sides by read-out devices 44 and 46.

The crystal 42 forms the first of a sandwich of four such crystals and the others are denoted by reference numerals 48, 50 and 52. Between 42 and 48 is a high-Z material such as W denoted by reference numeral 54 and a similar wedge of material 56 and 58 exists between the other crystals 48 and 50 and 50 and 52 respectively.

A low-Z absorption layer 60 absorbs X-rays which have penetrated the last of the crystal. Typically this is formed from aluminium as in FIG. 1.

Opposed lateral read-outs are provided for each of the crystals 48, 50 and 52 in the same way as 44 and 46 are provided for crystal 42.

In accordance with the invention the different outputs from the four different crystals 42, 48, 50 and 52 are added together to provide a combined output signal which will correspond to the high energy X-ray component for combination with the signal from the first crystal 32 which relates to the low energy X-ray component.

Although four crystals are shown in FIG. 2, it is to be understood that the invention is not limited to any particular number of crystals, and any number may be employed after the first thin crystal. A larger number of crystals may be particularly advantageous if higher energy X-rays are employed, eg 18-25 MeV, such as used in medical radiotherapy.

Figure 3:
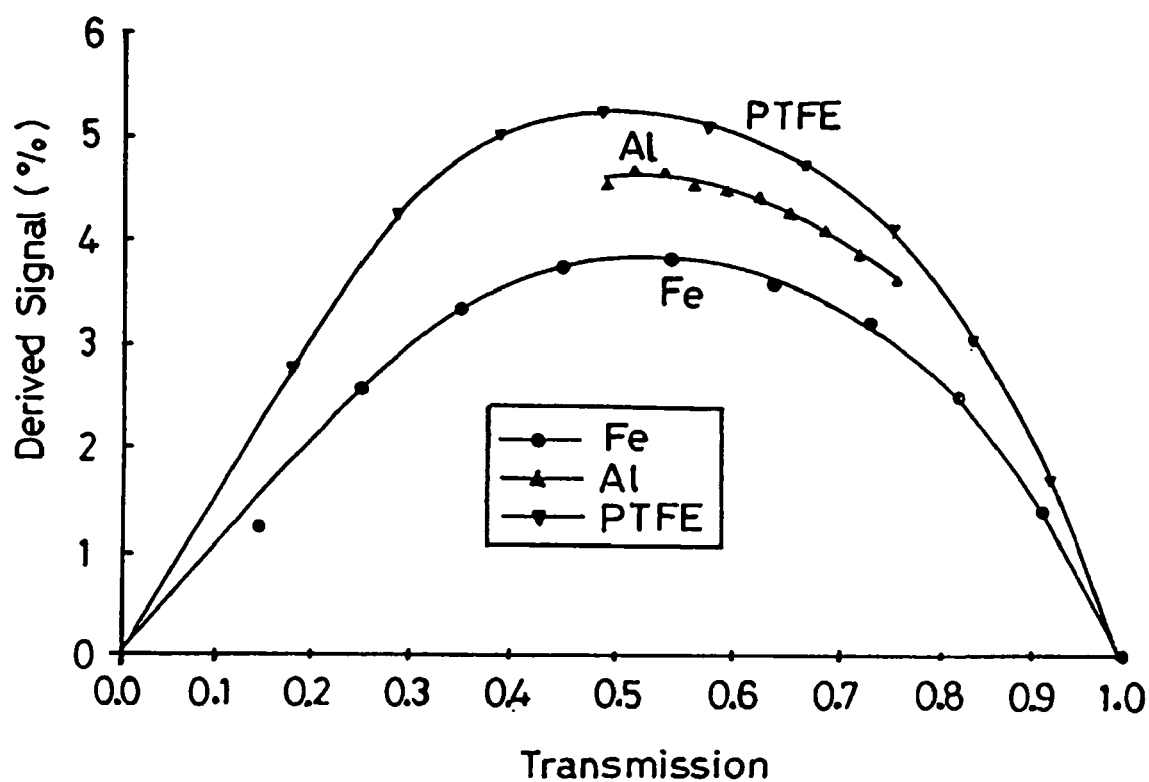
FIG. 3 illustrates MD curves obtained from a typical single detector element using three different materials for calibration.

FIG. 3 shows the signal derived from a single detector element (described as a Dexel), in percentage terms, plotted against the transmission T, using 10 MeV X-rays. The percentage is taken with respect to the bright field signals, ie with zero absorber in the beam.

Although in the examples given two pairs of read-out devices have been shown for each crystal, the invention is not limited to such arrangements. Thus for example, if a single read-out device for any of the crystals is adequate, that arrangement is also to be understood to be within the scope of the present disclosure.

The invention claimed is:

1. A material discrimination system including a high energy X-ray source, a first detector component in the form of a thin scintillation crystal for registering an amount of energy deposited by an X-ray that is essentially independent of the X-ray energy, a thicker one-piece downstream scintillation crystal, a low-Z converter situated between the thin crystal and the thicker crystal to stop electrons produced by X-ray interactions downstream of the thin crystal from being significantly backscattered into the thin crystal and prevent electrons leaving the thin crystal from returning and depositing more energy in the thin crystal, and a plurality of read-out devices for detecting light energy emitted by the crystals and generating respective electrical output signals in response thereto, wherein a pair of read-out devices is provided to read out from opposite sides of the thin crystal, and further pairs of read-out devices are provided to read out from opposite sides of the thicker crystal at different respective depths in the beam direction, and wherein the output signal from one read-out device of each pair is added to the output signal from the other read-out device of the pair on the opposite side of the crystal to reduce any left/right asymmetry in the output signals.

2. A material discrimination system as claimed in claim 1, wherein the low-Z converter is formed of aluminium.

3. A material discrimination system as claimed in claim 1, wherein behind the low-Z converter is located a high-Z, high density converter.

4. A material discrimination system as claimed in claim 3, wherein the high-Z converter is formed of tungsten.

5. A material discrimination system as claimed in claim 1, wherein each pair of read-out devices comprises a pair of photodiodes or a pair of optical fibres.

6. A material discrimination system as claimed in claim 1, wherein an absorber is located at the rear of a detector assembly.

7. A material discrimination system as claimed in claim 6, wherein the absorber is formed of aluminium.

* * * * *